(12) United States Patent
Tarler

(10) Patent No.: US 9,693,732 B1
(45) Date of Patent: Jul. 4, 2017

(54) ELECTRODE PATCH AND WIRELESS PHYSIOLOGICAL MEASUREMENT SYSTEM AND METHOD

(71) Applicant: Matthew D Tarler, Avon, OH (US)

(72) Inventor: Matthew D Tarler, Avon, OH (US)

(73) Assignee: Orbital Research Inc., Cleveland, OH (US)

( * ) Notice: Subject to any disclaimer, the term of this patent is extended or adjusted under 35 U.S.C. 154(b) by 0 days.

(21) Appl. No.: 14/837,432

(22) Filed: Aug. 27, 2015

Related U.S. Application Data

(63) Continuation of application No. 11/711,365, filed on Feb. 27, 2007, now Pat. No. 9,149,229, which is a continuation of application No. 10/879,666, filed on Jun. 29, 2004, now Pat. No. 7,206,630.

(51) Int. Cl.
| | |
|---|---|
| *A61B 5/06* | (2006.01) |
| *A61B 5/00* | (2006.01) |
| *A61B 5/0408* | (2006.01) |
| *A61B 5/0478* | (2006.01) |
| *A61B 5/0492* | (2006.01) |
| *A61B 5/0496* | (2006.01) |

(52) U.S. Cl.
CPC ......... *A61B 5/6833* (2013.01); *A61B 5/0006* (2013.01); *A61B 5/0478* (2013.01); *A61B 5/04085* (2013.01); *A61B 5/0492* (2013.01); *A61B 5/0496* (2013.01)

(58) Field of Classification Search
CPC ...... A61B 5/0006; A61B 5/6833; A61N 1/05; A61N 1/08; H04L 67/125
See application file for complete search history.

(56) References Cited

U.S. PATENT DOCUMENTS

| | | | | |
|---|---|---|---|---|
| 5,511,553 A | * | 4/1996 | Segalowitz .......... | A61B 5/0006 128/903 |
| 5,544,649 A | * | 8/1996 | David .................. | A61B 5/6887 128/904 |
| 7,020,508 B2 | * | 3/2006 | Stivoric ............... | A61B 5/0205 600/390 |

* cited by examiner

*Primary Examiner* — Rex R Holmes
(74) *Attorney, Agent, or Firm* — Brian Kolkowski

(57) ABSTRACT

The present invention is related, in general, to an electrode patch and/or a wireless system for measuring the physiological condition of a subject, and more particularly to an electrode patch for ECG monitoring. The present invention further includes a method of sensing, analyzing and/or transmitting or relaying a physiological signal. The wireless system and/or electrode patch of the present invention is preferably lightweight and compact. The electrode patch preferably additionally provides a low, power system for extended battery life and use. The electrode patch and wireless system of the present invention still further preferably allows for good and reliable measurement of physiological signals form the subject. The electrode patch is still preferably simple to apply as a single patch, but versatile enough to be reconfigured as more than one patch.

20 Claims, 12 Drawing Sheets

ELECTRODE PATCH AND WIRELESS PHYSIOLOGICAL MEASUREMENT SYSTEM AND METHOD

CROSS-REFERENCE TO RELATED APPLICATIONS

This application is a continuation of U.S. patent application Ser. No. 11/711,365 which was filed on Feb. 27, 2007 and issued as U.S. Pat. No. 9,149,229 on Oct. 6, 2015, and which was as a continuation of U.S. patent application Ser. No. 10/879,666, which was filed on Jun. 29, 2004, and which issued as U.S. Pat. No. 7,206,630 on Apr. 17, 2007.

The U.S. Government has a paid-up license in this invention and the right in limited circumstances to require the patent owner to license others on reasonable terms provided for by the terms of grant number 5R44HL065024-03 awarded by the National Institutes of Health.

BACKGROUND OF THE INVENTION

1. Field of the Invention

The present invention is related, in general, to an electrode patch and/or a wireless system for measuring the physiological condition of a subject, and more particularly to an electrode patch for ECG monitoring. The present invention further includes a method of sensing and analyzing a physiological signal.

2. Technical Background

Monitoring one or more physiological conditions of a patient is well known. Medical patient monitoring systems are highly sophisticated utilizing telemetry systems at a central receiving and monitoring station. ECG monitoring has the greatest applications.

According to present estimates, approximately 60 millions Americans have one or more types of cardiovascular disease including high blood pressure, coronary artery disease, stroke, rheumatic heart disease, congenital cardiovascular defects and congestive heart failure. Cardiovascular disease claims approximately one million lives in the United States each year, or approximately forty percent of all deaths. Since 1990, cardiovascular disease has been the number one killer in the United States every year other than 1918. More than 2,600 Americans die each day of cardiovascular disease, which is an average of 1 death every 33 seconds.

Because heart performance can deteriorate quickly, the key to effective cardiovascular disease management resides in early medical intervention. Patients often to not recognize subtle changes in cardiovascular disease symptoms and may not appreciate the importance of quickly reporting such changes to their physician. To make early intervention possible and prevent rehospitalization, healthcare providers need daily access to accurate information about patients' symptoms. There are many reasons a physician may want to monitor patients on a continuous or nearly continuous basis. These include the need to detect episodic arrhythmias, either to establish a diagnosis or to evaluate efficacy of therapy; the need to help evaluate syncope, in particular to detect any associated cardiac rhythm disorder or to assess therapy; the need to assess efficacy of therapy for atrial arrhythmias (this is especially important with atrial fibrillations in patients at risk for stroke or systemic embolism who can not take warfarin or similar drugs); the need in patients at increased risk for sudden arrhythmic death, particularly for example those patients with ventricular dysfunction who would benefit from prolonged (6 weeks to 6 months) ECG monitoring after serious events such as a myocardial infarction, an episode of cardiac decompensation, recent cardiac surgery or the onset of new therapy with an antiarrhythmic agent; and the need for providing patients with at home immediate access to 911 emergency help without patient action particularly for those patients who have had multiple myocardial infarctions.

A typical diagnostic process for any of these cardiovascular conditions may include one or more of the following tests: ECG; Holter monitor; external loop recorder; implantable loop recorder; tilt table test; electrophysiology study; and a stress test. An ECG can be performed in a physician's office or a hospital setting. It is unlikely, however, a patient will undergo many of the symptoms associated with these conditions such as for example syncope or fibrillation in those few minutes. A Holter monitor is a device that measures and records heart rhythm, usually over 1 day but occasionally for 2 or more days. Holter monitors can miss recording a critical moment when a diagnosis could be made because the event doesn't happen during the recording, or because the patient took the device off to sleep. This is particularly important where patients do not want to wear the device to work for fear of discrimination if their employer or fellow employees know they have a health problem. An external loop recorder is a device that monitors heart rhythm and rate for up to a month. During this test, the patient wears a device on the wrist, around the chest or in a pocket. The patient must press a button on the device to make a recording of the heart activity during the period the symptoms occur such as fainting. Unfortunately, this only occurs if the patient is sufficiently aware that the event took place. Furthermore, the information collected must be downloaded periodically making in more difficult for the patient to comply. Implantable loop recorders are relatively new devices. These devices suffer from these same drawbacks as well as the possibility of infection due to the invasive procedure used to implant the device. A tilt table test is used to simulate conditions that may cause fainting. It enables the physician to gauge how blood pressure, heart rate and rhythm respond to a change in position from lying down to standing. This test is expensive and is generally only done in a large or teaching hospital setting. An electrophysiology study is an expensive and invasive procedure. This procedure threads a catheter into the heart to record the heart's own electrical impulses and to assess the response to pacing and extra beats. Other tests such as cardiac stress tests are expensive and generally are performed in a hospital setting.

Traditional tests leave large numbers of patients with recurrent, unexplained, undiagnosed cardiac problems after undergoing these tests. The primary reasons these tests fall short are: 1) They only monitor the heart for a relatively limited amount of time, or 2) They require the patient to wear a device in their daily living that is embarrassing and inconvenient to wear, and/or that requires them to perform a task after experiencing a symptom. Therefore, there is a need for a diagnostic tool that allows one to continuously monitor the heart's rhythm and rate for long periods of time, on the order of several months or more, and requires no action by the patient at the time of fainting.

While a number of technologies have been developed to allow for patient monitoring at home or on the go, each of these technologies suffer from one or more major drawbacks. U.S. Pat. No. 5,458,124 to Stanko et al. describes an electrode and wireless transmitter system for use in measuring the physiological condition of a subject. The system in Stanko due to the rigidity of the system doesn't allow for good electrode contact with the patient's skin. Furthermore, the system in Stanko doesn't provide a good means for data error detection, nor in process adjustment by an external source. U.S. Pat. Nos. 5,862,803; 5,957,854; and U.S. Pat. No. 6,289,239 to Besson et al. provides for a wireless electrode system for measuring various body conditions. This system, however, is cumbersome, overly complex and limiting in that among other things it requires separate electronics for each electrode, as well as, a source of power external to the electrode. Because of the unique power requirements, this system presumably doesn't allow for remote wireless monitoring at any great distance thereby creating an invisible tether to the receiver and limiting the versatility of the system.

The wireless technologies outlined above are interesting, but are not applicable for the easy measurement physiological signals and transmission over long periods of time. A compact, wireless physiological monitoring technology is needed for this purpose. It is therefore, an object of this invention to provide an electrode patch and wireless system for such a purpose. It is a further object of this invention to provide an electrode patch and wireless system with a feasible battery system. It is still a further object of this invention to provide an electrode patch and wireless system that allows for good measurement from two or more electrodes. It is still further an object of this invention to provide an electrode patch and wireless system that provided for data error correction. It is still further an object of this invention to provide an electrode patch and wireless system, which utilizes dry physiological electrodes for detecting the physiological signals.

SUMMARY OF THE INVENTION

The present invention is related, in general, to an electrode patch and/or a wireless system for measuring the physiological condition of a subject, and more particularly to an electrode patch for ECG monitoring. The present invention further includes a method of sensing, analyzing and/or transmitting or relaying a physiological signal.

The wireless system and/or electrode patch of the present invention is preferably lightweight and compact. The electrode patch preferably additionally provides a low, power system for extended battery life and use. The electrode patch and wireless system of the present invention still further preferably allows for good and reliable measurement of physiological signals form the subject. The electrode patch is still preferably simple to apply as a single patch, but versatile enough to be reconfigured as more than one patch.

In one embodiment, the present invention includes an electrode patch for sensing a physiological signal from a subject, the electrode patch comprising a base having an upper and a lower surface, the lower surface of the base comprising at least two electrodes for placing on a subjects skin and for sensing of a physiological signal from the subject; one or more electronic components for receiving the physiological signal and transmitting a signal corresponding to the physiological signal to a receiving unit or remote communication station, the one or more electronic components being attached to the base; and at least two electrical pathways connecting the at least two electrodes to the one or more electronic components which are not used as a primary means to mechanically attach the one or more electronic components to the base.

In another embodiment, the present invention includes an electrode patch for sensing a physiological signal from a subject, the electrode patch comprising a base having an upper and a lower surface, the lower surface of the base comprising at least two electrodes for placing on a subjects skin and for sensing of a physiological signal from the subject; one or more electronic components for receiving the physiological signal and transmitting a signal corresponding to the physiological signal to a receiving unit or remote communication station, the one or more electronic components; at least two electrical pathways connecting to the at least two electrodes; and a fastener for attaching the one or more electronic components to the base and electrically connecting the at least two electrical pathways to the one or more electronic components.

In still another embodiment, the present invention includes an electrode patch for sensing a physiological signal from a subject, the electrode patch comprising a base having an upper and a lower surface, the lower surface of the base comprising at least two electrodes for placing on a subjects skin and for sensing of a physiological signal from the subject; and one or more electronic components for receiving the physiological signal from the at least two electrodes, transmitting a signal corresponding to the physiological signal to a receiving unit or remote communication station, and receiving a signal from a remote transmitter, the one or more electronic components being attached to the base.

In still another embodiment, the present invention includes a wireless system for monitoring at least one physiological condition of a subject, the system comprising an electrode patch comprising a base having an upper and a lower surface, the lower surface of the base comprising at least two electrodes for placing on a subjects skin and for sensing of a physiological signal from the subject; and one or more electronic components for receiving the physiological signal, transmitting a signal corresponding to the physiological signal to a receiving unit or remote communication station and receiving a signal from a remote transmitter, the one or more electronic components being attached to the base; and a receiving unit or remote communication station for receiving, re-transmitting and/or processing the signal corresponding to the physiological signal, the receiving unit or remote communication station comprising a computer, processor and/or one or more electronic parts.

In yet another embodiment, the present invention includes a method comprising the steps of sensing and analyzing a physiological signal comprising the steps of measuring a physiological signal from a subject; transmitting wirelessly the physiological signal from the subject to a remote communication station; and transmitting data formed in part from the physiological signal from the remote communication station wirelessly or via the internet to another computer or processor system.

In still yet another embodiment, the present invention includes a method comprising the steps of applying a wireless electrode patch to a subject; digitizing and/or analyzing a physiological signal measured from the subject with the electrode patch; transmitting wirelessly from the electrode patch the digitized and/or analyzed physiological signal from the subject to a remote communication station; and re-transmitting a signal based in part from the physiological signal from the remote communication station wirelessly or via the internet to another monitor, computer or processor system.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DESCRIPTION OF THE PREFERRED EMBODIMENT

Figure 1:
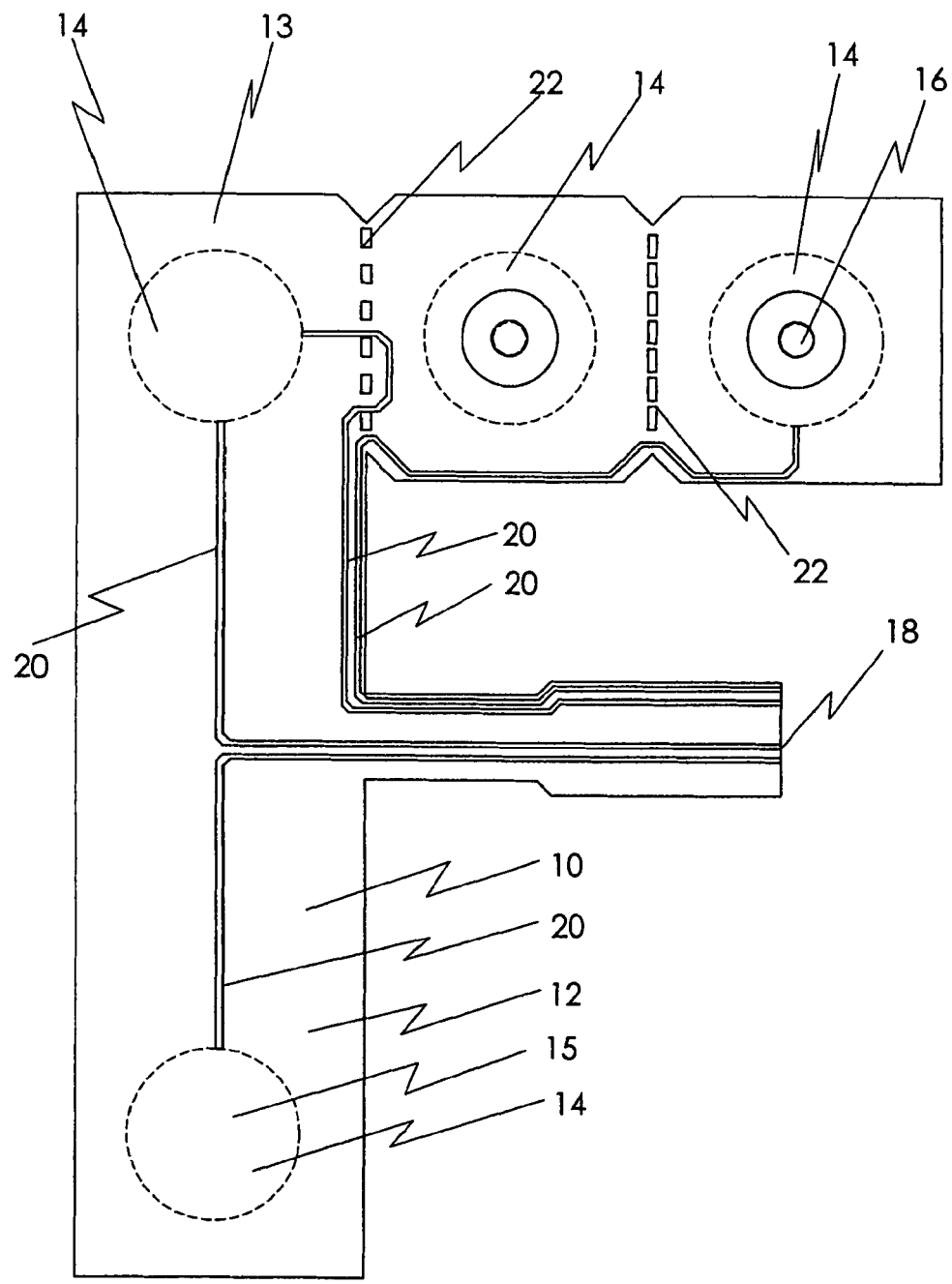
FIG. 1. Plan cross-sectional view of the base of one embodiment of an electrode patch.

The present invention is related, in general, to an electrode patch and/or a wireless system for measuring the physiological condition of a subject, and more particularly to an electrode patch for ECG monitoring. The present invention further includes a method of sensing and analyzing a physiological signal.

The electrode patch and the wireless system of the present invention are preferably used for sensing or detecting a physiological signal from a subject. The subject from which a physiological signal is measured being a human or other form of animal. The electrode patch and the wireless system of the present invention can be used in a variety of applications including but not limited to electrocardiography (ECG), electroencephalography (EEG), electrical impedance tomography (EIT), electromyography (EMG), and electro-oculography (EOG). Preferably, the electrode patch and the wireless system of the present invention is used for electrocardiography (ECG).

The electrode patch, which is a part of the wireless system of the present invention comprises a base having an upper and lower surface. The lower surface of the base comprising at least two electrodes. The electrodes are used for sensing a physiological signal from a subject. The electrode patch further comprises one or more electronic components. The one or more electronic components are used to receive the physiological signal from the at least two electrodes. The one or more electronic components also transmit or store a signal corresponding to the physiological signal to a remote receiving unit. Preferably, the one or more electronic components can further receive signals from one or more remote, receiving units. In a number of embodiments, the electrode patch further comprises at least two electrical pathways connecting to the at least two electrodes to one or more electronic components for receiving the physiological signal.

The electrical pathways are preferably attached to the base. More preferably, the electrical pathways are a line of conductive ink, which is printed on the upper surface of the base. Even more preferably, the electrical pathways are printed on the upper surface of the base and are drawn to a connector. This allows for separate production of the electronic components of the electrode patch and further for reuse or recycling of the electronic components. Also preferably, any of the electronic components and their electrical connections can be printed on the base of the electrode patch. The electrical pathways of the present invention are preferably greater than about 0.25 inches in length, more preferably greater than about 0.5 inches in length, and most preferably greater than about 1.0 inches in length. Preferably, the electrical pathways are made from some conductive ink or coating material.

The subject(s) referred to in the present invention can be any form of animal. Preferably the subject(s) are mammal, and most preferably human. The base having an upper and a lower surface can be made from any materials known to those skilled in the art. Preferably the base is made from a material which has the mechanical features necessary for the at least two electrodes and for attaching to the one or more electronic components. More preferably, the base is a laminate. Even more preferably, the base incorporates some type of foamed or cellular material that allows a certain flexibility and depth necessary for wells or depressions to hold conductive electrode gels or pastes. Preferably, the base comprises a flexible spacer layer with a modulus of elasticity of less than about 500,000 psi, more preferably less than about 100,000 psi, and most preferably less than about 30,000 psi. The spacer layer can be made from any polymer known to those skilled in the art. Preferably, the spacer layer is a foam or celled structure. Most preferably, the spacer layer is a closed cell structure, which doesn't allow for absorption of biological contaminants. Preferably the spacer layer of the base is between about 0.001 to about 0.3 inches thick, more preferably between about 0.01 to about 0.2 inches thick, and most preferably between about 0.03 to about 0.15 inches thick. If an adhesive is used to attach the electrode patch to the subject, preferably the adhesive is biologically compatible to the subject. More preferably, a pressure sensitive adhesive is used. Even more preferably, a removable pressure sensitive adhesive is used. The adhesives used include but are not limited to for example natural rubber, butyl, styrenic block copolymer, SBR, acrylics, and silicone based adhesives. Preferably, if a base laminate is used, the base laminate comprises a more rigid upper surface wherein the upper surface has an elastic modulus greater than that of the spacer layer. This allows for a better surface on which to attach the one or more electronic components of various embodiments of the present invention.

The lower surface of the base, preferably, comprises at least two electrodes, more preferably more than at least three electrodes, and most preferably more than at least four electrodes. The at least two electrodes can be any type of electrode known to those skilled in the art for sensing a physiological signal. Preferably, the at least two electrodes of the present invention can be conventional electrodes known to those skilled in the art comprising a sensing element and a conductive gel for transmitting the signal between the subjects skin and the sensing element; or dry electrodes comprising a penetrator for detecting physiological signals below the surface of the skin as a sensing element. Dry physiological recording electrodes of the type described in U.S. patent application Ser. No. 09/949,055 are herein incorporated by reference. Dry electrodes provide the advantage that there is no gel to dry out, no skin to abrade or clean, and that the electrode can be applied in hairy areas such as on an animal or on a male human's chest. Alternatively, the subject(s) skin may be mechanically abraded, or an amplified electrode may be used. Preferably, the at least two electrodes are one signal electrode and one reference electrode. The at least two electrodes don't have to be of the same type, i.e., for example one could be a conductive gel electrode and the other a dry electrode. The at least two electrodes can be any shape known to be useful to those skilled in the art. For example the electrodes can be circular or non-circular in shape. Preferably, the at least two electrodes are in close proximity with no more than 6 inches between each of their sensing elements or their closest sensing elements, more preferably with no more than 4 inches between each of their sensing elements or their closest sensing elements, and most preferably with no more than 2 inches between each of their sensing elements or their closest sensing elements.

The electrode patch is attached to the subject by any method or means known to those skilled in the art. By way of example but not limitation, the electrode patch may be attached to the subject by adhesive on the lower surface of the base, by adhesive on the electrodes on the lower surface of the base, by an elastomeric band that is attached to the based and about the subject, or some combination thereof.

The electrode patch further comprises one or more electronic components for detecting the physiological signal from the at least two electrodes. While some of the electronic components such as the battery or antenna may be separate from the other electronic components, and in the case of the antenna may be printed right onto the base. One or more of the electronic components are mechanically attached to the base. Preferably, the one or more electronic components are mechanically attached to the upper surface of the base. The one or more electronic components can be attached by any means known to those skilled in the art including but not limited to hooks, hangers, Velcro, clips and the like. The one or more electronic components are, however, preferably not attached to the base by the electrical pathways. If, however, this is not possible preferably the one or more electronic components are attached with a connecter that incorporates at least two electrical pathways.

The one or more electronic components for detecting the physiological signal from the at least two electrodes is a wireless device, which most preferably transmits the physiological signals to a remote receiving unit. Preferably, the one or more electronic components also filter (and possibly amplify) the detected signal, and more preferably convert this detected physiological signal, which is in an analog form into a digital signal for transmission to the remote receiving unit. The one or more electronic components are attached to the subject as part of the electrode patch. Further preferably, the one or more electronic components can receive a signal from the remote receiving unit or other remote transmitters. The one or more electronic components may include circuitry for but are not limited to for example electrode amplifiers, signal filters, analog to digital converter, RF output antenna, RF input antenna, RF output/ input antenna, subcarrier VCO, transmitter VCO, tuning crystal, phase-locked loop, frequency select switches, a DC power source and combinations thereof. The one or more electronic components may comprise one processing chip, multiple chips, single function components or combinations thereoof, which can perform all of the necessary functions of detecting the physiological signal from the electrode, transmitting a signal corresponding to the physiological signal to a receiving unit and optionally receiving a signal from a remote transmitter. These one or more electronic components can be assembled on a printed circuit board or by any other means known to those skilled in the art. Preferably, the one or more electronic components can be assembled on a printed circuit board or by other means so its imprint covers an area less than 4 in$^2$, more preferably less than 2 in$^2$, even more preferably less than 1 in$^2$, still even more preferably less than 0.5 in$^2$, and most preferably less than 0.25 in$^2$.

Preferably, the circuitry of the one or more electronic components is appropriately modified so as to function with any suitable miniature DC power source. More preferably, the DC power source is a battery. A preferred battery of the present invention are zinc-air hearing aid batteries. Zinc-air hearing aid batteries offer a high energy density and nearly constant output voltage during discharge, which is preferable. Preferably, a three-cell stack of zinc-air batteries is used, each cell offering a steady 1.2 V, and producing a stable and reliable 3.6 V. The most preferred battery of the present invention are Lithium-ion batteries. Lithium-ion batteries also offer a high energy density and nearly constant output voltage during discharge. Additionally, these commercially available batteries are readily available and inexpensive and a single battery produces slightly greater than 3 V, which is preferable. Alternatively, high frequency energy may be transmitted to the electrode patch from some external source to power the circuitry of the one or more electronic components through some type of capacitor.

Preferably, the circuitry of the one or more electronic components comprises data acquisition circuitry further including an electrode amplifier which detects the physiological signal from the at least two electrodes and integrates the detected physiological signals into a single signal and amplifies it to some power level. The data acquisition circuitry is designed with the goal of reducing size, lowering (or filtering) the noise, increasing the DC offset rejection and reducing the system's offset voltages. The data acquisition circuitry may be constrained by the requirements for extremely high input impedance, very low noise and rejection of very large DC offset and common-mode voltages, while measuring a very small signal of interest. Additional constraints arise from the need for a "brick-wall" style input protection against ESD and EMI. The exact parameters of the design, such as input impedance, gain and passband, can be adjusted at the time of manufacture to suit a specific application via a table of component values to achieve a specific full-scale range and passband.

More preferably, a low-noise, lower power instrumentation amplifier is used. The inputs for this circuitry is guarded with preferably, external ESD/EMI protection, and very high-impedance passive filters to reject DC common-mode and normal-mode voltages. Still preferably, the instrumentation amplifier gain can be adjusted from unity to approximately 100 to suit the requirements of a specific application. If additional gain is required, it preferably is provided in a second-order antialias filter, whose cutoff frequency can be adjusted to suit a specific application, with due regard to the sampling rate. Still preferably, the reference input of the instrumentation amplifier is tightly controlled by a DC cancellation integrator servo that uses closed-loop control to cancel all DC offsets in the components in the analog signal chain to within a few analog-to digital converter (ADC) counts of perfection, to ensure long term stability of the zero reference.

Preferably, the physiological signal is converted to a digital form. This can be achieved with an electronic component or processing chip through the use of an ADC. More preferably, the ADC restricts resolution to 12-bits due to the ambient noise environment in such chips. Despite this constraint, the ADC remains the preferable method of choice for size-constrained applications such as with the present invention unless a custom data acquisition chip is used because the integration reduces the total chip count and significantly reduces the number of interconnects required on the printed circuit board.

Preferably, the circuitry of the one or more electronic components comprises a digital section. Part of this circuitry may include one or more chips preconfigured to perform some or all of the digital processing for use with existing wireless protocols including but not limited to wireless local area networks (IEEE 802.11 including WiFi), wireless personal area networks (IEEE 802.15 including Bluetooth and ZigBee), wireless metropolitan area networks (IEEE 802.16) or others known to those skilled in the art. More preferably, the heart of the digital section is the Micro-Chip™ PIC 16LC771 microcontroller or other comparable microcontrollers including microcontrollers from competing companies including Atmel and Texas Instruments. The preferable MicroChip™ PIC 16LC771 microcontroller or other comparable microcontroller would contain sufficient data and program memory, as well as peripherals, which allow the entire digital section as well as the ADCs to be neatly bundled into a single carefully programmed processing chip. Still preferably, the onboard counter/timer sections are used to produce the data acquisition timer, and can further be used to measure the VCO frequency and to confirm synthesizer lock. Still preferably, an onboard synchronous serial (SPI) port is used to control the synthesizer, to generate a RF data stream, and to communicate with external test equipment. Also preferably, an onboard main oscillator generates not only the microcontroller clock, but also the reference clock for the synthesizer. Additional digital outputs are used to control specific functions. Still preferably, one ADC input is dedicated to measurement of the VCO tune voltage to allow for automation of the final testing, and a separate function multiplexed onto this same pin allows limited direct control of the VCO tune voltage during automated final testing.

The synthesizer can induce distortion in the transmitted digital data when the data does not contain exactly equal numbers of ones and zeroes over a prolonged interval. This distortion arises because the synthesizer sees the modulation as error to be served out, and fights the modulation as it attempts to steer the VCO back to the nominal frequency. Preferably, the reference oscillator has the ability to modulate the reference frequency with any low-frequency content of the final transmitted digital data, with one of the results being that the reference and the VCO move in concert during modulation and therefore do not distort the data, and the low-frequency content of the designed data packet format should result in only minimal distortion. Optionally, this capability can be removed to reduce the imprint of the printed circuit board holding the one or more electronic components.

Preferably, the circuitry for the one or more electronic components is designed to provide for communication with external quality control test equipment prior to sale, and more preferably with automated final test equipment. In order to supply such capability without impacting the final size of the finished unit, one embodiment is to design a communications interface on a separate PCB using the SPI bus with an external UART and level-conversion circuitry to implement a standard RS-232 interface for connection to a personal computer or some other form of test equipment. The physical connection to such a device requires significant PCB area, so preferably the physical connection is designed to keep the PCB at minimal imprint area. More preferably, the physical connection is designed with a break-off tab with fingers that mate with an edge connector. This allows all required final testing and calibration of the electrode patch, including the programming of the processing chip memory, can be carried out through this connector, with test signals being applied to the analog inputs through the normal connections which remain accessible in the final unit. By using an edge fingers on the production unit, and an edge connector in the production testing and calibration adapter, the electrode patch can be tested and calibrated without leaving any unnecessary electronic components or too large a PCB imprint area on the final unit.

Preferably, the circuitry for the one or more electronic components comprises nonvolatile, rewriteable memory. Alternatively, if the circuitry for the one or more electronic components doesn't comprise nonvolatile, rewriteable memory then an approach should be used to allow for reprogramming of the final parameters such as radio channelization and data acquisition and scaling. Without nonvolatile, rewriteable memory, the program memory can be programmed only once. Therefore one embodiment of the present invention involves selective programming of a specific area of the program memory without programming the entire memory in one operation. Preferably, this is accomplished by setting aside a specific area of program memory large enough to store several copies of the required parameters. Procedurally, this is accomplished by initially programming the circuitry for the one or more electronic components with default parameters appropriate for the testing and calibration of the electrode patch. When the final parameters have been determined, the next area is programmed with these parameters. If the final testing and calibration reveals problems, or some other need arises to change the values, additional variations of the parameters may be programmed. The firmware of various embodiments of the present invention scans for the first blank configuration block and then uses the value from the preceding block as the operational parameters. This arrangement allows for reprogramming of the parameters up to several dozen times, with no size penalty for external EEPROM or other nonvolatile RAM. The circuitry for the one or more electronic components has provisions for in-circuit programming and verification of the program memory, and this is supported by the breakoff test connector. The operational parameters can thus be changed up until the time at which the test connector is broken off just before shipping the final unit. Thus the manufacturability and size of the circuitry for the one or more electronic components is optimized.

Preferably the circuitry of the one or more electronic components includes an RF transmitter. Still preferably includes a custom voltage controlled oscillator (VCO) made up of discrete electronic components, and a phase-locked loop (PPL) synthesizer built around commercially available electronic components. Still preferably, the whole radio section of the circuitry can be powered down independently of the digital section components. Still further preferably, the synthesizer is controlled by the firmware via the SPI bus, and uses a crystal oscillator to derive a precision clock.

In these embodiments, the VCO design is unique in several ways. A buffer is preferably required between the core VCO active element and the antenna, to minimize pulling of the VCO frequency by physical movement at or near the antenna. Still preferably, the VCO itself uses a negative-resistance oscillator configuration. Still preferably, this is a stacked configuration to allow sharing between the VCO and the buffer. Still preferably, this configuration allows for two or more different configurations of the buffer with negligible size impact on the imprint of the circuitry of the one or more electronic components. In one configuration, the VCO and buffer are in a cascade configuration (common base amplifier), such that the buffer provides voltage gain and buffering. In another configuration, the configuration becomes a common-emitter buffer, with the potential to allow firmware control of the transmitted power during PLL lock by reducing the gain of the buffer during lock. Preferably, this capability is provided with no size or power impact in the common-emitter configuration and reduces the potential for interference with other units during unit startup. On the other hand, the cascade configuration preferably is more resistant to antenna pulling, so precharge of the tune voltage and careful sequencing and timing of the startup are required to prevent interference.

Preferably, tuning of the VCO is performed by using a unique architecture that minimizes power consumption while significantly reducing noise compared to more conventional approaches such as using a varactor to perform tuning in response to an applied voltage. Preferably, in various embodiments of the present invention, the PLL applies a tuning voltage to the top side of a varactor, reversing biasing of the varactor to the level required to achieve a desired oscillation frequency. Conventional designs mix the modulation with this tune voltage to modulate the carrier produced by the VCO. However, this mixing normally requires a summing junction plus a buffer, and the buffer generates significant 1/F noise, seriously degrading the phase noise performance of the VCO. In addition, the required swing of the modulation voltage is orders of magnitude smaller than that of the tune voltage. Preferably in various embodiments of the present invention, only the PLL tune voltage is injected at the top of the varactor, and the modulation voltage is injected at the bottom of the varactor. By pre-inverting the modulation voltage, a bias voltage is achieved across the varactor that is the arithmetic sum of the tune voltage and the modulation voltage without the undesirable interactions of the conventional approaches. Because the required swing of the modulation voltage is very small, a resistive divider can be used as the last step in applying the modulation voltage, thus keeping the signal amplitude very large right up until the final division, forcing any accompanying noise to also be divided down before application to the varactor. This enhances the signal-to-noise ratio in the modulation voltage. Additionally because the required swing is very small, the division ratio in the final divider is large, allowing for very low current draw while still providing extremely low Thevenin equivalent resistance and very low thermal noise at this sensitive node.

Another feature of the circuitry of the one or more electronic components preferably is an antenna. The antenna, preferably, is designed onto the upper surface of the base of the electrode patch and is integrated in the rest of the circuitry. The antenna can be configured in a number of ways, for example as a single loop, dipole, dipole with termination impedance, lagarithmic-periodic, dielectric, strip conduction or reflector antenna. The antenna is designed to include but not be limited to the best combination of usable range, production efficiency and end-system usability. Preferably, the antenna consists of one or more conductive wires or strips, which are arranged in a pattern to maximize surface area. The large surface area will allow for lower transmission outputs for the data transmission. The large surface area will also be helpful in receiving high frequency energy from an external power source for storage. Optionally, the radio transmissions of the present invention may use frequency-selective antennas for separating the transmission and receiving bands, if a RF transmitter and receiver are used on the electrode patch, and polarization-sensitive antennas in connection with directional transmission. Polarization-sensitive antennas consist of, for example, thin metal strips arranged in parallel on an insulating carrier material. Such a structure is insensitive to or permeable to electromagnetic waves with vertical polarization; waves with parallel polarization are reflected or absorbed depending on the design. It is possible to obtain in this way, for example good cross polarization decoupling in connection with linear polarization. It is further possible to integrate the antenna into the frame of a processing chip or into one or more of the other electronic components, whereby the antenna is preferably realized by means of thin film technology. The antenna can serve to just transfer electrode patch data or for both transferring data to and for receiving control data received from a remote communication station which can include but is not limited to a wireless relay, a computer or a processor system. Optionally, the antenna can also serve to receive high-frequency energy (for energy supply or supplement). In any scenario, only one antenna is required for transmitting data, receiving data and optionally receiving energy. Optionally, directional couples can be arranged on the transmitter outputs of the electrode patch and/or the remote communication station. The couplers being used to measure the radiated or reflected radio wave transmission output. Any damage to the antenna (or also any faulty adaptation) thus can be registered, because it is expressed by increased reflection values.

An additional feature of the present invention is an optional identification unit. By allocating identification codes—a patient code (for each electrode patch), the remote communication station is capable of receiving and transmitting data to several subjects, and for evaluating the data if the remote communication station is capable of doing so. This is realized in a way such that the identification unit has a control logic, as well as a memory for storing the identification codes. The identification unit of the electrode patch is preferably programmed by radio transmission of the control characters and of the respective identification code from the programming unit of the remote communication station to the electrode patch. More preferably, the electrode patch comprises switches in the electrode patch as programming lockouts, particularly for preventing unintentional reprogramming of the electrode patch.

In any RF link, errors are an unfortunate and unavoidable problem. Analog systems can often tolerate a certain level of error. Digital systems, however, while being inherently much more resistant to errors, also suffer a much greater impact when errors occur. Thus the present invention when used as a digital system, preferably includes an error control subarchitecture. Preferably, the RF link of the present invention is digital. RF links can be one-way or two-way. One-way links are used to just transmit data. Two-way links are used for both sending and receiving data.

If the RF link is one-way error control, then this is preferably accomplished at two distinct levels, above and beyond the effort to establish a reliable radio link to minimize errors from the beginning. At the first level, there is the redundancy in the transmitted data. This redundancy is performed by adding extra data that can be used at the remote communication station or at some station to detect and correct any errors that occurred during transit across the airwaves. This mechanism known as Forward Error Correction (FEC) because the errors are corrected actively as the signal continues forward through the chain, rather than by going back to the transmitter and asking for retransmission. FEC systems include but are not limited to Hamming Code, Reed-Solomon and Golay codes. Preferably, a Hamming Code scheme is used. While the Hamming Code scheme is sometimes maligned as being outdated and underpowered, the implementation in certain embodiments of the present invention provides considerable robustness and extremely low computation and power burden for the error correction mechanism. FEC alone is sufficient to ensure that the vast majority of the data is transferred correctly across the radio link. Certain parts of the packet must be received correctly for the receiver to even begin accepting the packet, and the error correction mechanism in the remote communication station reports various signal quality parameters including the number of bit errors which are being corrected, so suspicious data packets can be readily identified and removed from the data stream.

Preferably, at a second, optional level, an additional line of defense is provided by residual error detection through the use of a cyclic redundancy check (CRC). The algorithm for this error detection is similar to that used for many years in disk drives, tape drives, and even deep-space communications, and is implemented by highly optimized firmware within the electrode patch processing circuitry. During transmission, the CRC is first applied to a data packet, and then the FEC data is added covering the data packet and CRC as well. During reception, the FEC data is first used to apply corrections to the data and/or CRC as needed, and the CRC is checked against the message. If no errors occurred, or the FEC mechanism was able to properly correct such errors as did occur, the CRC will check correctly against the message and the data will be accepted. If the data contains residual errors (which can only occur if the FEC mechanism was overwhelmed by the number of errors), the CRC will not match the packet and the data will be rejected. Because the radio link in this implementation is strictly one-way, rejected data is simply lost and there is no possibility of retransmission.

More preferably, the RF link utilizes a two-way (bi-directional) data transmission. By using a two-way data transmission the data safety is significantly increased. By transmitting redundant information in the data emitted by the electrodes, the remote communication station is capable of recognizing errors and request a renewed transmission of the data. In the presence of excessive transmission problems such as, for example transmission over excessively great distances, or due to obstacles absorbing the signals, the remote communication station is capable of controlling the data transmission, or to manipulate on its own the data emitted by the electrode patch. With control of data transmission it is also possible to control or re-set the parameters of the electrode patch, e.g., changing the transmission channel. This would be applicable for example if the signal transmitted by the electrode patch is superimposed by other sources of interference then by changing the channel the remote communication station could secure a flawless and interference free transmission. Another example would be if the signal transmitted by the electrode patch is too weak, the remote communication station can transmit a command to the electrode patch increasing its transmitting power. Still another example would be the remote communication station causing the electrode patch to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements of the electrode patch. This also reduces the energy requirements of the electrode patch, thereby providing longer battery life. Another advantage of a two-way, bi-directional digital data transmission lies in the possibility of transmitting test codes in order to filter out external interferences such as, for example, refraction or scatter from the transmission current. In this way, it is possible to reconstruct falsely transmitted data. Due to the safe and effective one-way and two-way transmission of the various embodiments of the present invention between the electrode patch and the remote communication station, the present invention is particularly suitable for use at home or work, such as for example monitoring infants or heart patients, especially where no technical personnel are available.

The remote communication station of various embodiments of the present invention can be any device known to receive RF transmissions used by those skilled in the art to receive transmissions of physiological data from the electrode patch. The remote communication station by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the remote communication station can further transmit data both to another device and/or back to the electrode patch. Further optionally, two different remote communication stations can be used, one for receiving transmitted physiological data from the electrode patch and another for sending data to the electrode patch. For example, with the wireless physiological monitoring system of the present invention, the remote communication system of the present invention can be a wireless router, which establishes a broadband internet connection with the electrode patch and transmits the physiological signal to a remote internet site for analysis, preferably by the subject's physician. Another example is where the remote communication system is a PDA, computer or cell phone, which receives the physiological data transmission from the electrode patch, optionally re-processes the information, and re-transmits the information via cell towers, land phone lines or cable to a remote site for analysis. Another example is where the remote communication system is a computer or processor, which receives the physiological data transmission from the electrode patch and displays the data or records it on some recording medium, which can be displayed or transferred for analysis at a later time.

Preferably, the wireless monitoring system of the present invention can be used to notify a doctor, monitoring service or an emergency medical dispatch team of a problem with the subject. To provide for the maximum flexibility of the subject preferably, the subject can be monitored by application of a wireless electrode patch to the subject. Preferably, the electrode patch provides electronics and a battery such that the battery or patch only need to be changed no more than 1 time a day, more preferably no more than once every two days, and most preferably no more than once every four days. The wireless electrode patch then digitizes and/or analyzing a physiological signal measured from the subject with the electrode patch. This digitized or analyzed physiological signal is then transmitting wirelessly from the electrode patch to a remote communication station. This remote communication station allows the subject wide movement. Preferably, the remote communication station can pick up and transmit signals from distances of greater than about 5 feet from the subject, more preferably greater than about 10 feet from the subject, even more preferably greater than about 20 feet from the subject, still even more preferably greater than about 50 feet from the subject, still even more preferably greater than about 200 feet from the subject, and most preferably greater than about 500 feet from the subject. The remote communication station is used to re-transmit the signal based in part from the physiological signal from the remote communication station wirelessly or via the internet to another monitor, computer or processor system. This allows the physician or monitoring service to review the subjects physiological signals and if necessary to make a determination, which could include dispatching help.

Referring now to the drawings, FIG. 1 is a planar cross-sectional view of the base of an electrode patch. In FIG. 1, the electrode patch 10 comprises a base 12 having an upper 13 and lower surface (not shown). The base 12 comprises at least two electrodes 14 for placing on a subject's skin and for sensing a physiological signal from the subject. The at least two electrodes 14 can either be attached to the lower surface of the base 12, be incorporated into the lower surface of the base 12, or be formed into the base 12 itself. If the electrodes 14 are formed into the base itself then preferably the base 12 is a laminate. If the base 12 is a laminate then preferably the base 12 comprises a lower surface consisting of an adhesive layer, at least one spacer layer and an upper surface 13. The base is preferably multiple layers, and most preferably is a laminate. The electrode patch 10 in FIG. 1 consists of four electrodes 14—with one of those electrodes being used as a reference electrode 15. The electrode patch 10 also comprises at least one electrical pathway 20, the at least one electrical pathway for connecting the electrode 14 to a connector 18 or one or more electronic components (not shown) for transmitting the physiological signal detected by the electrodes 14 to a remote communication station (not shown). In addition to the electrical pathways 20, optionally the electrodes 14 may include other types of connectors such as the button type connector 16 or other mechanical connectors 16. This embodiment of the electrode patch 10 further comprises a mechanical weak point 22 built into the base 12 to allow for separation of one of the electrodes 14 from the base 12.

Figure 2:
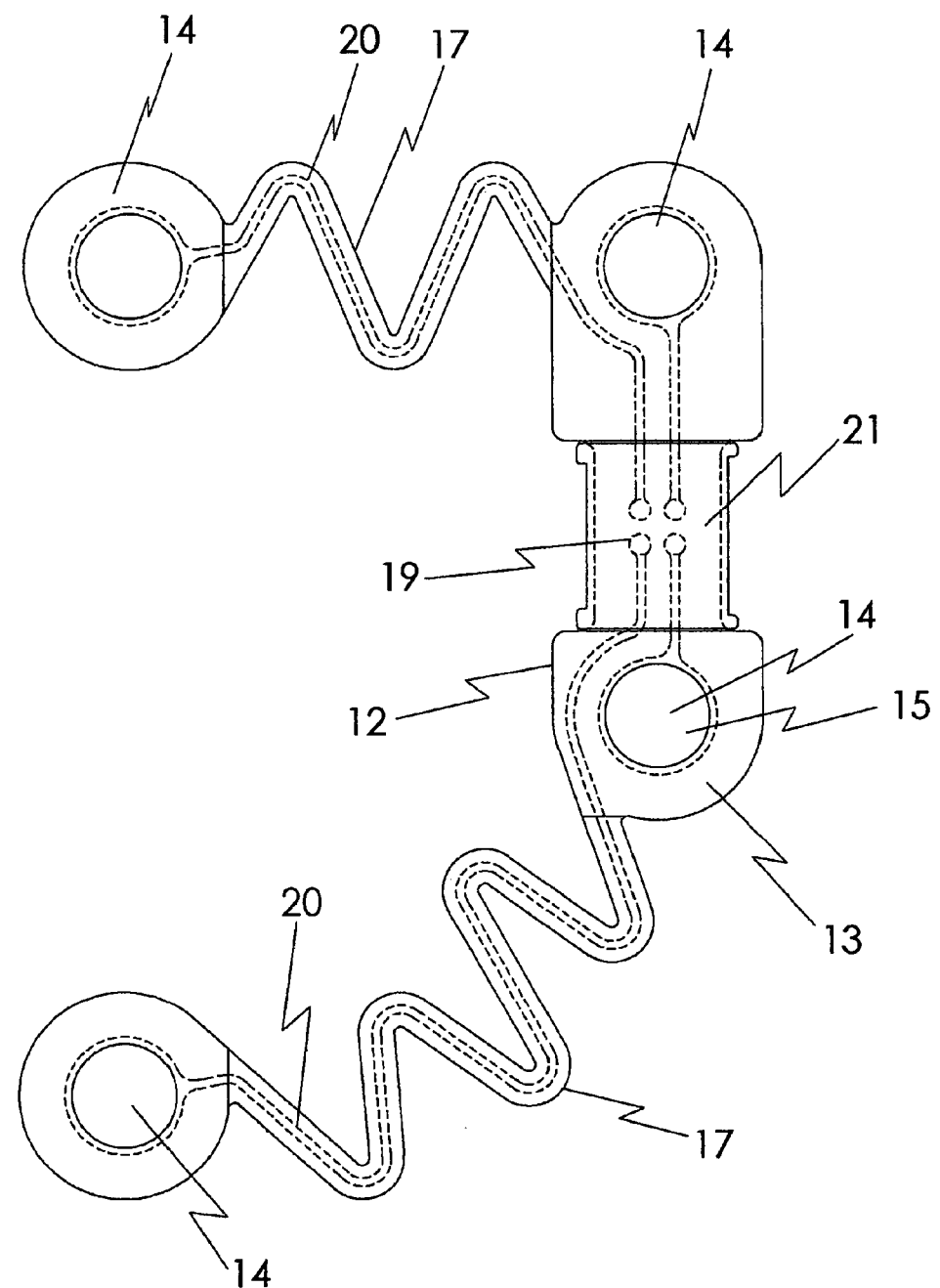
FIG. 2. Plan cross-sectional view of the base of another embodiment of an electrode patch.

FIG. 2 is a plan cross-sectional view of another embodiment of the base laminate used in the electrode patch of the present invention. In FIG. 2, the base laminate 12 comprises an upper 13 and a lower surface (not shown). The base 12 comprises at least two electrodes 14 for placing on a subject's skin and for sensing a physiological signal from the subject. The at least two electrodes 14 can either be attached to the lower surface of the base 12, be incorporated into the lower surface of the base 12, or be formed into the base 12 itself. If the electrodes 14 are formed into the base itself then preferably the base 12 is a laminate. If the base 12 is a laminate then preferably the base 12 comprises a lower surface consisting of an adhesive layer, at least one spacer layer and an upper surface 13. The base is preferably multiple layers, and most preferably is a laminate. The base laminate 12 in FIG. 2 consists of four electrodes 14—with one of those electrodes being used as a reference electrode 15. The base laminate 12 also comprises at least one electrical pathway 20, the at least one electrical pathway for connecting the electrode 14 to a connector (not shown) or one or more electronic components (not shown) for transmitting the physiological signal detected by the electrodes 14 to a remote communication station (not shown). The base laminate 12 further contains two flexible arms 17 which allow for versatility in placement of the electrode patch 10 and for use with varying size subjects. This embodiment of the base laminate 12 provides for a connector (not shown) which snaps or connects over a spring portion 21 of the laminate. The spring portion further comprises electrical contacts 19 which connect the electrode patch 10 electrical components (not shown) with preferably the base laminate. The electrical components being housed in the connector.

Figure 3:
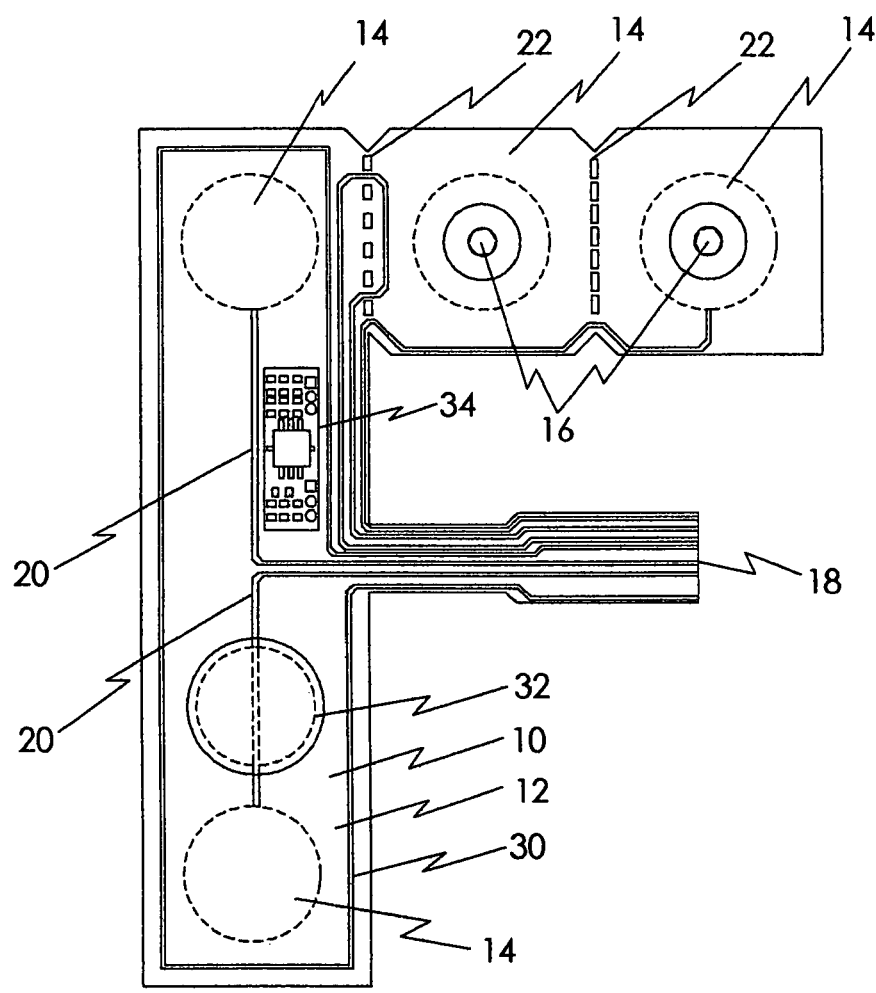
FIG. 3. Plan cross-sectional view of an electrode patch utilizing base from FIG. 1.

FIG. 3 is a planar cross-sectional view an electrode patch. In addition to the features disclosed in FIG. 1 for the base, the embodiment of the electrode patch 10 shown in FIG. 3 includes one or more electronic components 34 further including a battery 32 and a single loop antenna 30.

Figure 4:
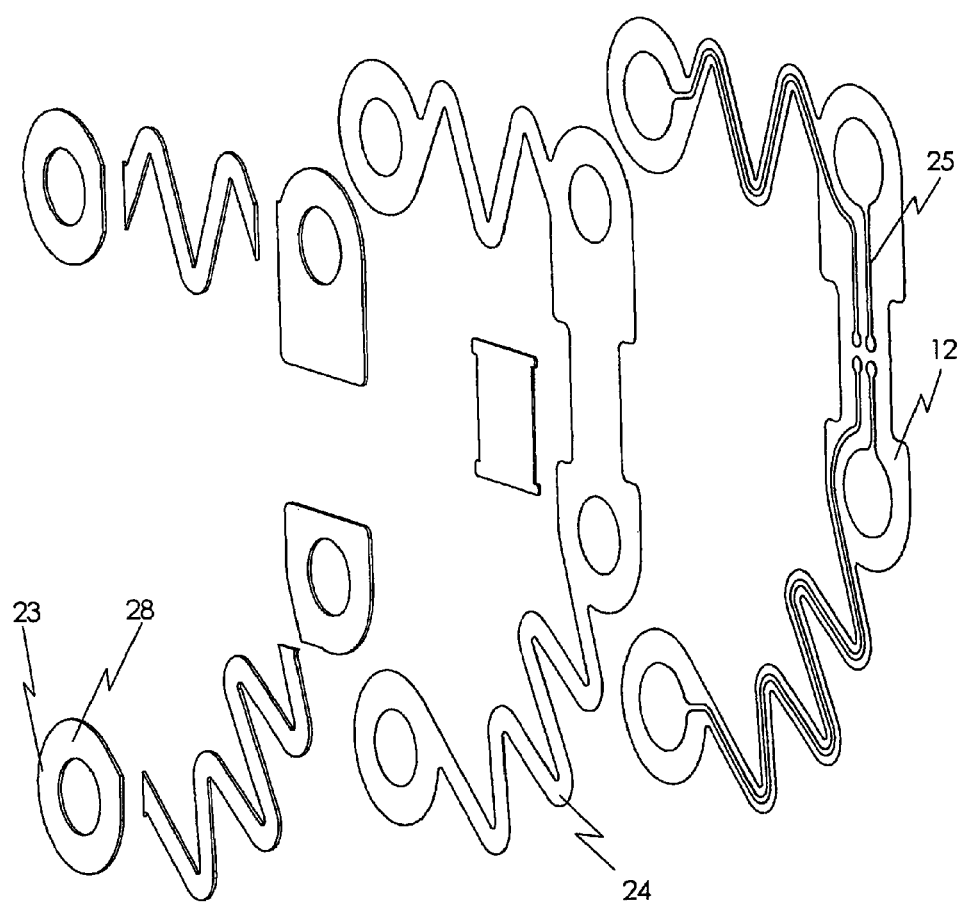
FIG. 4. Exploded view of base laminate from FIG. 2.

FIG. 4. is an exploded view of the base laminate from FIG. 2. The base laminate 12 in this embodiment used for an electrode patch comprises an adhesive layer (not shown) a bottom layer 23 with a bottom surface 28, spacer layer 24, and a top layer 25 with an upper surface (not shown). The layers forming the base laminate can be any materials known to those skilled in the art. Preferably, the materials are those approved by the FDA for these types of applications. For this particular embodiment, preferably the adhesive layer 23 is formed from a removable/releasable type pressure sensitive adhesive. The space layer 24 is preferably formed from a low modulus polyurethane or some other thermoplastic material selected for its ability to be laminated, soft texture for patient comfort and suitability for other aspects of the particular applications of the present invention. Attached to the lower surface of the adhesive layer 23 or disposed within the spacer layer 24 are at least two electrodes 14. The electrodes 14 in this particular embodiment are pre-gelled and incorporate a hypo-allergenic, silver/silver-chloride gel. The electrodes 14 are formed on the top layer 25 with the bottom layer 23 and spacer layer 24 providing a well to hold the silver/silver chloride gel.

Figure 5A:
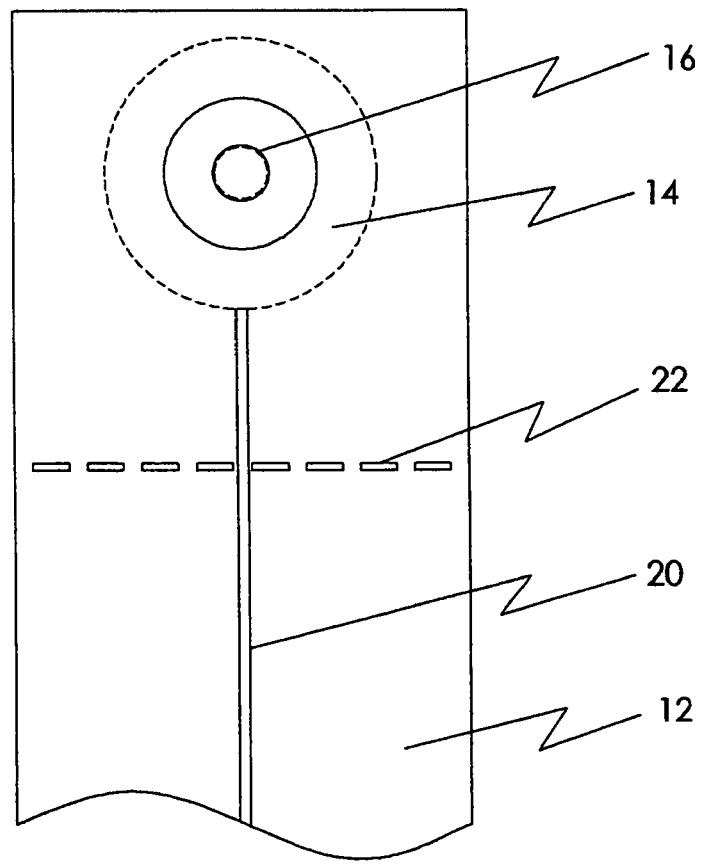
FIGS. 5A-C. Plan cross-sectional views of three embodiments of the reconfigurable electrical pathways of an electrode patches.
Figure 5B:
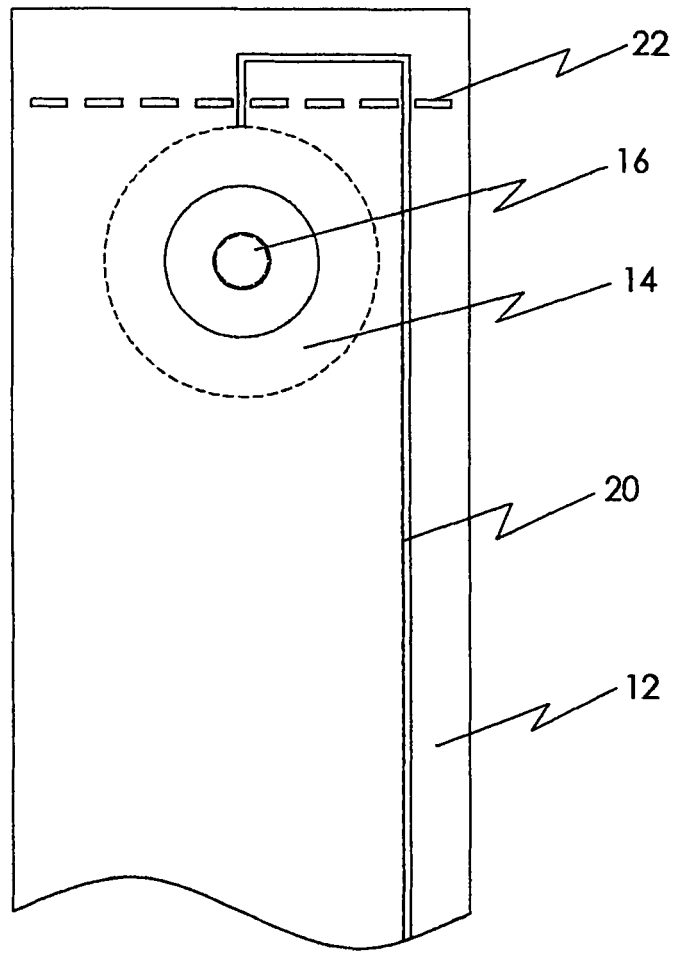
Figure 5C:
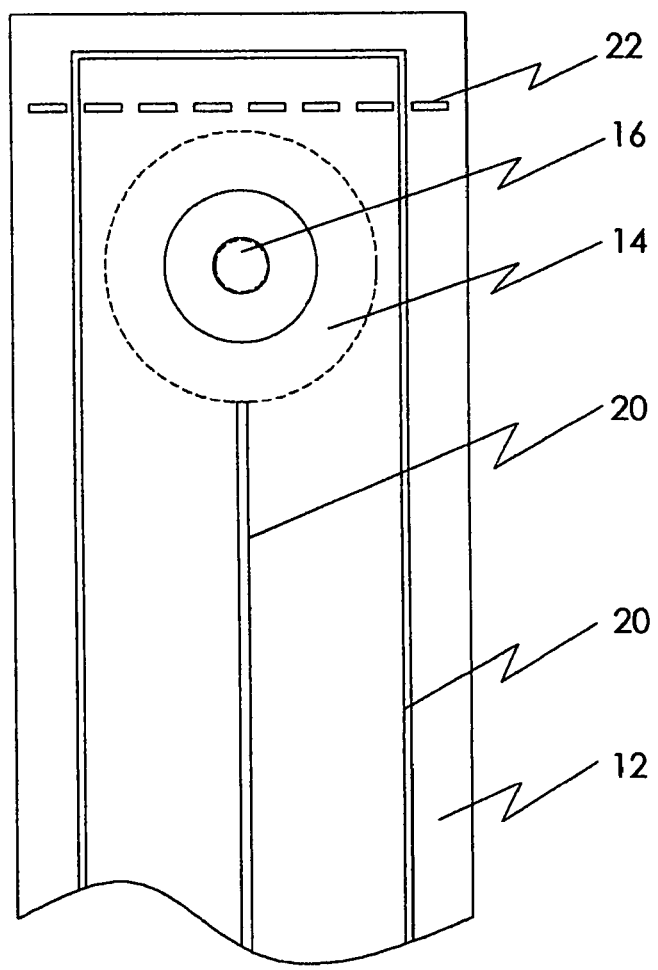

FIGS. 5A, 5B and 5C are planar cross-sectional views of three embodiments of the reconfigurable electrical pathways of the electrode patches of the present invention. FIG. 5 A) is an electrode portion 14 of the base 12 of an electrode patch (not shown). The electrode 14 in this embodiment having both a mechanical connection 16 providing a potential electrical pathway, and an electrical pathway 20 wherein the electrical pathway 20 connects the electrode 14 to a connector (not shown) or directly to the electronic components (not shown) of the electrode patch. A mechanical weak-point 22 further being incorporated into the base to allow for separation of the electrode 14 from the base, and in this particular embodiment, which breaks or disconnects the electrical pathway 20 connecting the electrode 14 to the connector or electronic components. FIG. 5 B) is another embodiment of an electrode portion 14 of the base 12 of an electrode patch. In this embodiment, the mechanical weak-point 22 allows the electrical pathway 20 connecting the electrode 14 to the connector or electronic components to be broken or disconnected, without separating the electrode 14 from the base 12. FIG. 5 C) is another embodiment of an electrode portion 14 of the base laminate 12 of an electrode patch. In this embodiment, there is an additional electrical pathway 20 such as an antenna or connecting to another electrode wherein the mechanical weak-point 22 allows this electrical pathway to be broken or disconnected.

Figure 6:
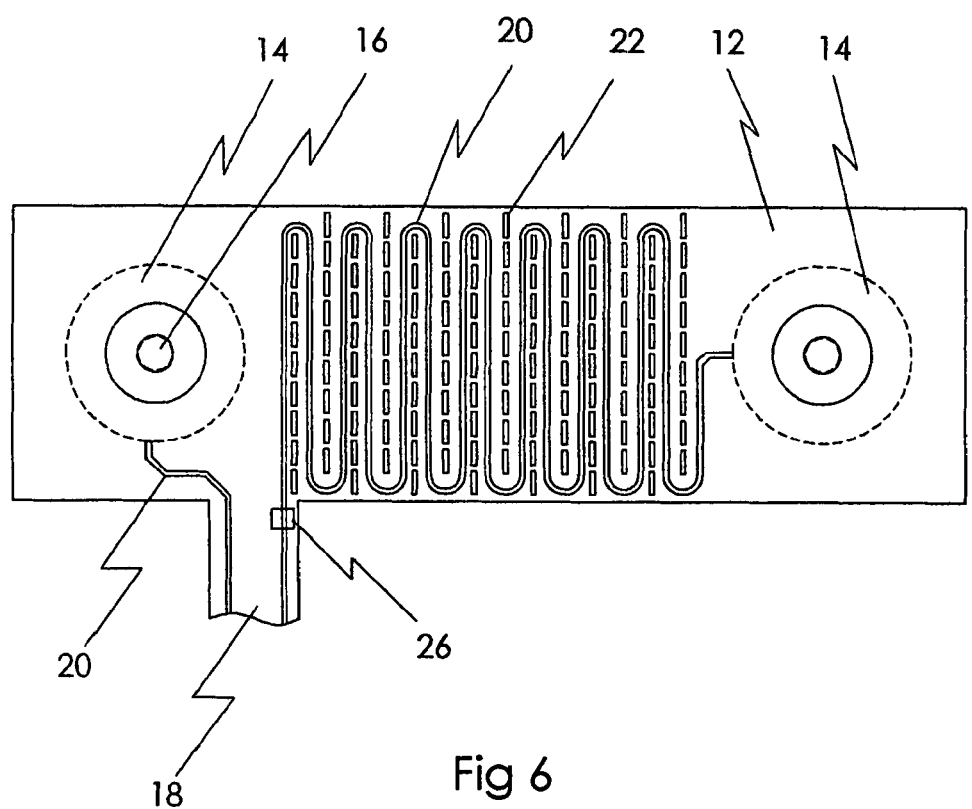
FIG. 6. Plan cross-sectional view of another embodiment of a reconfigurable electrode of the present invention.

FIG. 6 is a plan cross-sectional view of another embodiment of a reconfigurable electrode of the base of the electrode patch. In this embodiment, there are first and second electrodes, each electrode 14 being connected by an electrical pathway 20 to a connector 18 there being further one or more mechanical weak-points built into the base 12 wherein a certain portion of the base 12 can be separated without breaking either electrical pathway 20. In this particular embodiment one of the electrical pathways 20 is permanently affixed or connected to the base 12 after a certain electrical pathway connection point 26, but rather is a coiled or looped wire, which will enable the second electrode to be moved a distance from the first electrode after separation from the base allowing for different configurations of the electrode patch (not shown).

Figure 7:
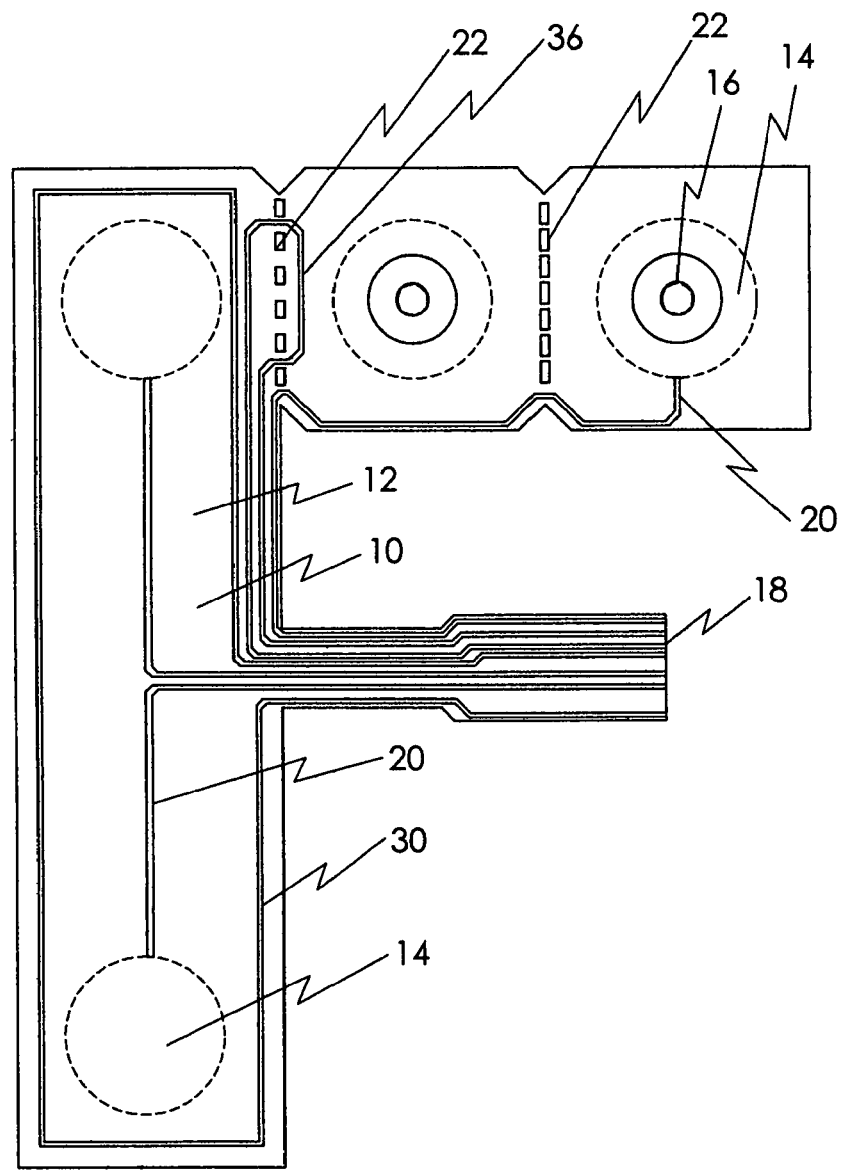
FIG. 7. Plan cross-sectional view of another embodiment of the base of an electrode patch.

FIG. 7 is a plan cross-sectional view of another embodiment of the base of an electrode patch. In addition to the features disclosed and described in FIG. 1 for the base, the embodiment of the electrode patch 10 shown in FIG. 6 includes an additional electrical pathway 36, which can be broken or disconnected by tearing or separating the base at one of the mechanical weak points 22 and hence the configuration change can be detected by the electronics attached to connector 18.

Figure 8:
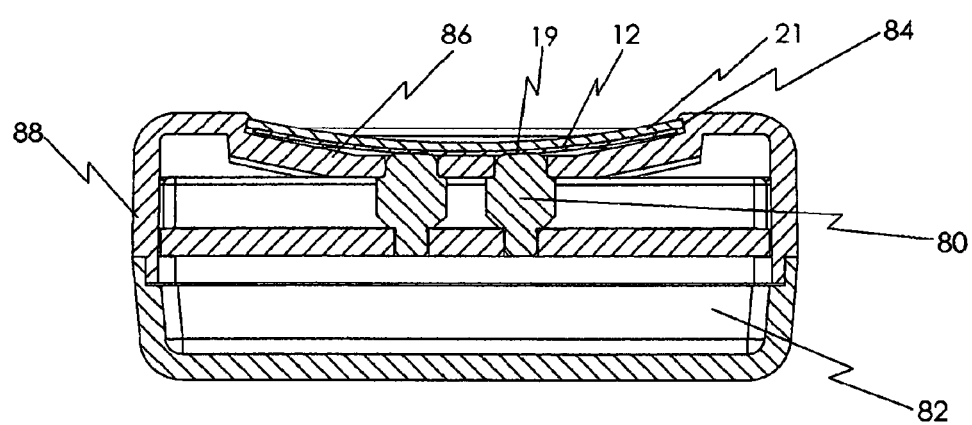
FIG. 8. Plan cross-sectional view of one embodiment of a connector used with base laminate described in FIGS. 2 and 4.

FIG. 8 is a plan cross-sectional view of one embodiment of a connector which is embedded into the housing for one or more electronic components, and can be used with a base laminate such as described in FIGS. 2 and 4. The housing 88 with the embedded connector region 86 provides a locking mechanism 84 for holding the spring portion 21 of the base laminate 12. The connector region 86 further provides one or more electrical contact pads which connect the electrical components (not shown) in the housing 88 with the electrical contacts 19 of the base laminate 12. The connector 86 in this embodiment uses electrical contact pads 80 to make such connection.

Figure 9:
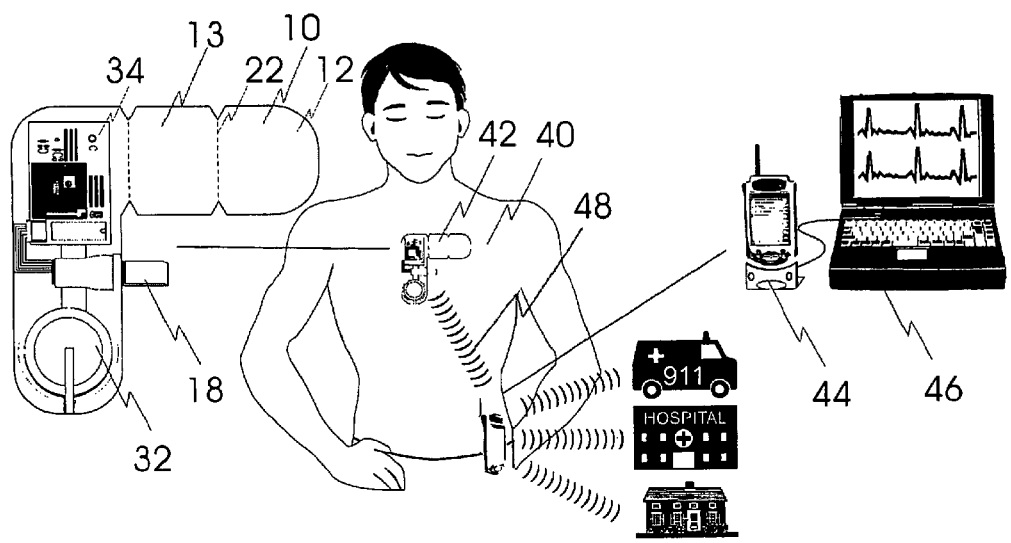
FIG. 9. Schematic representation of one embodiment of a wireless monitoring system of the present invention.

FIG. 9 is a schematic representation of one embodiment of the wireless monitoring system of the present invention. In FIG. 7, the subject 40 has an electrode patch 10 placed upon his or her chest 42, and attached by adhesive or other means, in order to monitor the physiological electrical signals from the subject's heart. The electrode patch 10 is one embodiment of the present invention described elsewhere in this application. The electrode patch 10 comprises a base 12 having an upper 13 and lower (not shown) surface and includes at least two electrodes (not shown) for placing on the subject's 40 skin. The electrode patch 10 further comprising one or more electronic components 34 including in this embodiment a battery 32. The one or more electronic components for receiving a physiological signal from the electrodes placed on the subject and for transmitting a signal corresponding to the physiological signal to a receiving unit 44, or remote communications station or device. The corresponding signal being transferred preferably via radio wave 48. The receiving unit 44 being a PDA, cell phone or some other type of device which can relay and/or process the received signal and optionally transmit instructions back to the electrode patch 10. In this embodiment the receiving unit 44 is a PDA which in turn is connected to a computer monitor 46 for processing the radio wave 48 signal and making decisions on whether to re-transmit the signal to another remote location such as a doctor's office or some other monitoring service, and whether to transmit a return signal to the one or more electronic components 34 of the electrode patch 10.

Figure 10:
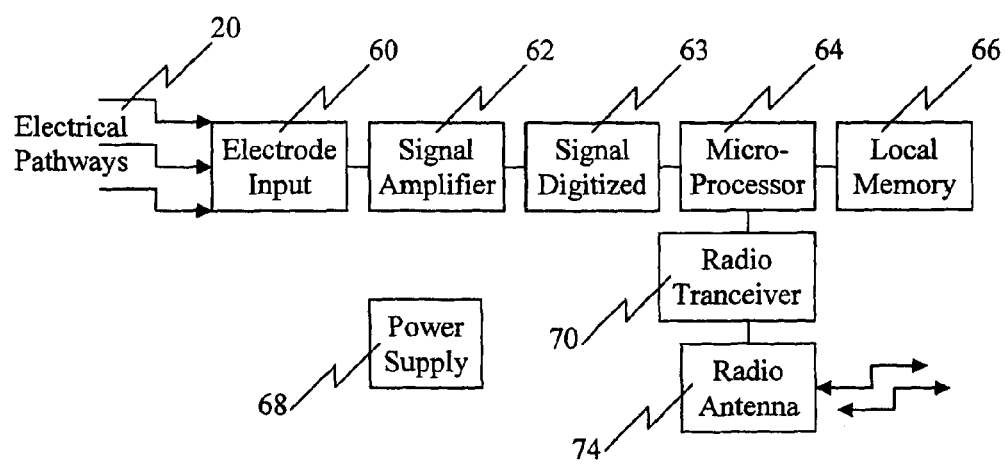
FIG. 10. Flow diagram of one embodiment of the one or more electronic components for the various devices and systems of the present invention.

FIG. 10 is a flow diagram for one embodiment of the one or more electronic components described for the present invention. In this flow diagram, the electrical pathways 20 carry an electrical signal from the electrodes to the electrical components. The electrode input 60 is then amplified with a signal amplifier 62 and digitized 63 for further processing with a computer or microprocessor 64. The computer or microprocessor 64 contains local memory 66. The processed physiological signal is passed to a radio transceiver 70 and broadcast via radio antenna 74 for further analysis or transmission. The electrical components are powered by a power supply 68 which can be either AC or DC and preferably is a battery.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A wireless system for sensing at least two different types of electrophysiological signals from a subject, the system comprising:
   a laminate base having an upper and a lower surface, the lower surface adapted for placing against a subject's skin, the laminate base comprising a spacer layer, an adhesive, and at least two electrodes adapted to be placed on the subject's skin and for sensing at least two different types of electrophysiological signals from the subject;
   one or more electronic components adapted to receive and filter at least two different types of electrophysiological signals from the at least two electrodes, to digitize the filtered signal(s) corresponding to the at least two different types of electrophysiological signals, and to wirelessly transmit the digitized signal(s) to a receiving unit, the one or more electronic components being attached to the base;
   at least two electrical pathways connecting the at least two electrodes to the one or more electronic components;
   a battery adapted to power the one or more electronic components; and
   a receiving unit that is a cell phone adapted to receive the digitized signal or signals corresponding to the at least two different types of electrophysiological signals.

2. The wireless system of claim 1, further comprising a RF transmitter comprising a polarization-sensitive antenna on the upper surface of the laminate base, the antenna comprising one or more conductive wires or strips arranged to maximize surface area and is adapted to transmit and receive signals, a voltage controlled oscillator (VCO), and a buffer between the antenna and VCO, and the wireless system further comprising memory adapted for programming the one or more electronic components.

3. The wireless system of claim 1, wherein the one or more electronic components include an electrode amplifier adapted to detect at least two channels of at least one type of electrophysiological signal from the at least two electrodes, to integrate the at least two channels of the detected electrophysiological signal into a single combined electrophysiological signal for, and to amplify the combined electrophysiological signal.

4. The wireless system of claim 3, wherein the one or more electronic components include an identification unit adapted to allocate an identification or patient code to the one or more electronic components and to allow the receiving unit or remote communication station to receive from and transmit data to multiple wireless systems.

5. The wireless system of claim 3, wherein the electrode amplifier is a low noise, low power instrumentation amplifier.

6. The wireless system of claim 2, wherein the RF transmitter comprises a digital bi-directional radio frequency (RF) link adapted to transmit redundant information to correct for errors in data transmission.

7. The wireless system of claim 6, wherein the VCO is configured in a stacked negative-resistance oscillator configuration and is in a cascade configuration with the buffer.

8. A wireless system for sensing at least two different types of electrophysiological signals from a subject, the system comprising:
a base having an upper and a lower surface, the lower surface adapted for placing against a subject's skin, the base comprising a spacer layer, an adhesive, and at least two dry electrodes adapted to be placed on the subject's skin and for sensing at least two different types of electrophysiological signals from the subject;
one or more electronic components adapted to receive and filter at least two different types of electrophysiological signals from the at least two dry electrodes, to digitize the filtered signal(s) corresponding to the at least two different types of electrophysiological signals, and to wirelessly transmit the digitized signal(s) to a receiving unit, the one or more electronic components being attached to the base;
at least two electrical pathways connecting the at least two electrodes to the one or more electronic components;
a battery adapted to power the one or more electronic components; and
a receiving unit that is a cell phone adapted to receive the signal or signals corresponding to the at least two different types of electrophysiological signals.

9. The wireless system of claim 8, further comprising a RF transmitter comprising a polarization-sensitive antenna on the upper surface of the laminate base, the antenna comprising one or more conductive wires or strips arranged to maximize surface area and is adapted to transmit and receive signals, a voltage controlled oscillator (VCO), and a buffer between the antenna and VCO, and the wireless system further comprising memory adapted for programming the one or more electronic components.

10. The wireless system of claim 8, wherein the one or more electronic components include an electrode amplifier adapted to detect at least two channels of at least one type of electrophysiological signal from the at least two electrodes, to integrate the at least two channels of the detected electrophysiological signal into a single combined electrophysiological signal for, and to amplify the combined electrophysiological signal.

11. The wireless system of claim 10, wherein the one or more electronic components include an identification unit adapted to allocate an identification or patient code to the one or more electronic components and to allow the receiving unit or remote communication station to receive from and transmit data to multiple wireless systems.

12. The wireless system of claim 10, wherein the electrode amplifier is a low noise, low power instrumentation amplifier.

13. The wireless system of claim 9, wherein the RF transmitter comprises a digital bi-directional radio frequency (RF) link adapted to transmit redundant information to correct for errors in data transmission.

14. The wireless system of claim 13, wherein the VCO is configured in a stacked negative-resistance oscillator configuration and is in a cascade configuration with the buffer.

15. A method of sensing electrophysiological signals from a subject comprising the steps of:
applying a patch to a subject, the patch comprising a laminate base, the base further comprising a spacer layer, an adhesive, and at least two electrodes adapted for placing on the subject's skin for sensing at least two different types of electrophysiological signals from the subject, one or more electronic components adapted to receive and filter at least two different types of electrophysiological signals from the at least two electrodes, to digitize the filtered signal(s) corresponding to the at least two different types of electrophysiological signals, and to wirelessly transmit through radio frequency the digitized signal(s) to a receiving unit or remote communication station;
re-transmitting the signal, wirelessly transmitted through radio frequency to the receiving unit or remote communication station by cell towers, land phone lines or cable; and
receiving the re-transmitted wireless signal for monitoring or analysis by a processor, a doctor or a monitoring service,
wherein the one or more electronic components of the wireless system utilize a two-way radio frequency data transmission with the receiving unit or remote communication station and the two-way radio transmission is used to reprogram the one or more electronic components.

16. The method of claim 15, wherein the one or more electronic components include an electrode amplifier adapted to detect at least two channels of at least one type of electrophysiological signal from the at least two electrodes, to integrate the at least two channels of the detected electrophysiological signal into a single combined electrophysiological signal for, and to amplify the combined electrophysiological signal.

17. The method of claim 16, wherein the one or more electronic components have a patient code, and the receiving unit identifies the patient code and receives and transmits data to multiple wireless systems.

18. The method of claim 16, wherein the electrode amplifier is a low noise, low power instrumentation amplifier.

19. The method of claim 16, further comprising the step of transmitting redundant information via a digital bi-directional radio frequency (RF) link to correct for errors in data transmission.

20. The method of claim 19, comprising the step of transmitting with the one or more electronic components a signal to notify a doctor, a monitoring service or an emergency medical dispatch team of a problem with the subject.

* * * * *